US008852246B2

(12) United States Patent
Hansson (10) Patent No.: US 8,852,246 B2
(45) Date of Patent: Oct. 7, 2014

(54) DEVICE FOR INTERNAL FIXATION OF THE BONE FRAGMENTS IN A RADIUS FRACTURE

(75) Inventor: Henrik Hansson, Vreta Kloster (SE)

(73) Assignee: Swemac Innovation AB, Linkoping (SE)

( * ) Notice: Subject to any disclaimer, the term of this patent is extended or adjusted under 35 U.S.C. 154(b) by 313 days.

(21) Appl. No.: 12/999,326

(22) PCT Filed: Jun. 17, 2009

(86) PCT No.: PCT/SE2009/050759
§ 371 (c)(1),
(2), (4) Date: Jan. 27, 2011

(87) PCT Pub. No.: WO2010/002333
PCT Pub. Date: Jan. 7, 2010

(65) Prior Publication Data
US 2011/0112583 A1    May 12, 2011

(30) Foreign Application Priority Data
Jul. 1, 2008  (SE) ...................................... 0801559

(51) Int. Cl.
*A61B 17/80*    (2006.01)
*A61B 17/86*    (2006.01)
*A61B 17/17*    (2006.01)

(52) U.S. Cl.
CPC ........... *A61B 17/8061* (2013.01); *A61B 17/863* (2013.01); *A61B 17/8057* (2013.01); *A61B 17/808* (2013.01); *A61B 17/1728* (2013.01)
USPC ........... 606/286; 606/281; 606/282; 606/287; 606/297

(58) Field of Classification Search
USPC ............ 606/64, 280, 281, 282, 286, 287, 291
See application file for complete search history.

(56) References Cited

U.S. PATENT DOCUMENTS

| 5,197,966 A | 3/1993 | Sommerkamp |
| 6,096,040 A | 8/2000 | Esser |
| 8,157,803 B1* | 4/2012 | Zirkle et al. .................... 606/64 |
| 2004/0193164 A1 | 9/2004 | Orbay |
| 2007/0073298 A1 | 3/2007 | Beutter et al. |
| 2009/0312803 A1* | 12/2009 | Austin et al. .................. 606/305 |
| 2009/0326591 A1* | 12/2009 | Spencer, Jr. .................. 606/282 |
| 2010/0030277 A1* | 2/2010 | Haidukewych et al. ...... 606/286 |

FOREIGN PATENT DOCUMENTS

| CN | 2006-087530 | 4/2006 |
| DE | 102005043285 | 1/2007 |
| WO | 2004/107957 | 12/2004 |
| WO | 2005/037114 | 4/2005 |
| WO | 2008036016 | 3/2008 |

* cited by examiner

*Primary Examiner* — Andrew Yang
*Assistant Examiner* — Olivia C Chang
(74) *Attorney, Agent, or Firm* — Tarolli, Sundheim, Covell & Tummino LLP (57) ABSTRACT

The present invention relates to a device for internal fixation of the bone fragments (2, 3) in a radius fracture (4). The device comprises at least one body (1) for abutment against the bone fragments (2, 3) in the radius fracture (4), and fixing elements (6, 7) which are intended to be locked to the body for fixation of said bone fragments. The body (1) itself has in a distal end portion (1*a*) at least two predrilled holes (8) for fixing elements (6), and in a proximal end portion (1*b*) at least two predrilled holes (9) for fixing elements (7). To allow effective optimum internal fixation of the bone fragments in the radius fracture, the predrilled holes (8, 9) run obliquely relative to a longitudinal axis (L) of the body (1) so that all of the fixing elements (6, 7) which, after the body has been caused to abut against the bone fragments (2, 3) in the radius fracture (4), are introduced into said bone fragments through holes (8, 9) in the body's distal end portion (1*a*) and proximal end portion (1*b*) cross the radius fracture (4) as viewed in the transverse direction of the body. Each fixing element (6, 7) has at least one fixing portion (10; 10*a*, 10*b*) for locking the fixing element in the bone fragments (2, 3) in the radius fracture (4) and for locking the fixing element to the body (1).

21 Claims, 6 Drawing Sheets

DEVICE FOR INTERNAL FIXATION OF THE BONE FRAGMENTS IN A RADIUS FRACTURE

BACKGROUND TO THE INVENTION

The present invention relates to a device for internal fixation of the bone fragments in a radius fracture.

This device comprises at least one body for abutment against the bone fragments in the radius fracture, and fixing elements which are intended to be locked to the body for fixation of said bone fragments. The body of said device has in a distal end portion at least two predrilled holes for fixing elements, and in a proximal end portion at least two predrilled holes for fixing elements.

Treatment of radius fractures has been a problem both because of the frequency of the injury and because of the difficulty of treating it. The object of the treatment is to restore the congruence and anatomy of the joint, minimise the risk of arthritis and maximise the mobility of the joint.

There are currently a number of possibilities for treating radius fractures.

Closed resetting entails manually resetting or aligning the broken bone and applying a plastercast on the arm. This prevents trauma relating to surgery and is less expensive for the care system. However, it also involves immobility due to the plaster until the bone fragments have healed, which may result in considerable stiffness not confined solely to the wrist and the forearm. The arm being rendered immobile often causes elderly persons considerable stiffness in the fingers, the elbow and the shoulder. The technique is also confined to the simplest and most stable patterns of fracture.

External fixation entails using relatively large-diameter pins introduced into metacarpal bones of the fingers and into the radius above the fracture. The pins are thereafter connected to a rod or frame. Two pins are usually placed in the hand and two in the radius. The frame may also be used for drawing the wrist apart in order to sustain the fracture resetting. External fixation has the disadvantage that the wrist and the hand are kept rigid by the frame, and pins through the skin tend to irritate the tendons and cause cicatrisation. These problems together cause considerable stiffness in both the wrist and the fingers, with loss or impairment of gripping function. Infections may also occur. External fixation does not effect any anatomical resetting of the bone fragments. External fixation is used mainly in severely comminuted fragmented fractures.

Open resetting entails making an incision above the wrist, resetting the bone fragments and using plates, screws or pins as necessary. Open resetting and internal fixation are not commonly used on radius fractures. There is risk of tendon cicatrisation, friction and stiffness. The blood supply to the bone fragments may be disturbed, which may delay or actually prevent their growing together. Drilling holes in, and screwing screws into, small and brittle bone fragments often causes further fragmentation of the latter, thereby further hampering anatomical resetting. Most bone fragments and displacements in ordinary radius fractures are situated on the dorsal side and the irregularity of the radius in this region combines with the many tendons situated close to the bone on this side to make it undesirable to place plates and screws dorsally. As the fractures often comprise a number of small fragments which need resetting, treatment by fixation with plates and screws is difficult.

Percutaneous pinning entails placing small rigid pins through the bone fracture fragments. The pins may be introduced directly through the skin under radiography. Pinning by a percutaneous or limited open technique results in internal fixation of the fracture with a certain further stability internally which is not achieved when the fracture is treated with plastercast only. As the bone fragments are often small and the bone brittle, small-diameter pins are more suitable for the fixation than screws. However, a stable bone adjacent to the bone fragment is required for fastening the pin. If the stable piece of bone is at some distance from, and at an awkward angle to, the bone fragment which is to be pinned, there is great risk that the pin may bend or be displaced. Another problem is that there is often no stable bone element in which to fasten the pin. The use of pins with a tendency to bend or be displaced also means that pinning is rarely done without a plastercast.

BRIEF SUMMARY OF THE INVENTION

The object of the present invention is to propose a device which allows effective optimum internal fixation of the bone fragments in a radius fracture.

This object is achieved by means of the device defined in the introduction. The predrilled holes in the body of the device run obliquely relative to a longitudinal axis of the body so that all of the fixing elements which, after abutment of the body against the bone fragments in the radius fracture, are introduced through holes in the body's distal end portion and proximal end portion and into said bone fragments cross the radius fracture as viewed in the transverse direction of the body. Each fixing element in said device has at least one fixing portion for locking the fixing element in the bone fragments in the radius fracture and for locking the fixing element to the body.

The device according to the present invention thus comprises a small number of parts which are easy to apply. The surgical operation becomes easy to perform with one or two very short incisions and the configuration of the device is such that the fixing elements can be placed in such a way as to achieve very stable fixation of the radius fracture.

Advantageous further versions of the device according to the present invention are defined in the subclaims.

Other objects and advantages of the invention will be apparent to one skilled in the art who examines the attached drawings and the following detailed description of preferred embodiments of it.

DETAILED DESCRIPTION OF PREFERRED EMBODIMENTS OF THE INVENTION

The device for internal fixation of the bone fragments in a radius fracture according to the present invention comprises, as already indicated, at least one body 1 for abutment against bone fragments 2 and 3 in the fracture 4 in the radius 5, and fixing elements 6 and 7 intended to be locked to the body for fixation of said bone fragments.

The body 1 is of elongate substantially platelike shape and size optimally suited to the intended application. The body 1 has with advantage a shape curving in the longitudinal direction corresponding to the shape of the radius 4. If so desired, the body 1 may be so configured as to be particularly suitable for right and left hands respectively and may also be made in different lengths. The body 1 may also be made in any thickness appropriate to purpose, e.g. about 2 mm or about 3 mm (FIGS. 10 and 11 and FIGS. 1-9 respectively). The body 1 may be made of polyethylene, e.g. UHMWPE (ultra high molecular weight polyethylene), in order by frictional locking to contribute to effective locking of the fixing elements 6, 7 to the body, and because this material is transparent to radiography. The body is of low weight (about 15 g if made of the material indicated). However, other materials may also be relevant, e.g. metals or metal alloys, provided that they have characteristics desired for the purpose.

According to the invention, the elongate body 1 has in a distal end portion 1a at least two predrilled holes 8 for fixing elements 6, and in a proximal end portion 1b at least two, in the version depicted three, predrilled holes 9 for fixing elements 7. According to the invention, the predrilled holes 8, 9 run obliquely relative to a longitudinal axis L (FIG. 4) of the body 1 so that all of the fixing elements 6 and 7 respectively which, after the body has been caused to abut against the bone fragments 2, 3 in the radius fracture 4, are introduced into said bone fragments through holes 8 and 9 respectively in the body's distal portion end 1a and proximal end portion 1b cross said radius fracture 4 as viewed in the transverse direction of the body. The result is great stability of the fixation of the radius fracture 4.

Figure 1:
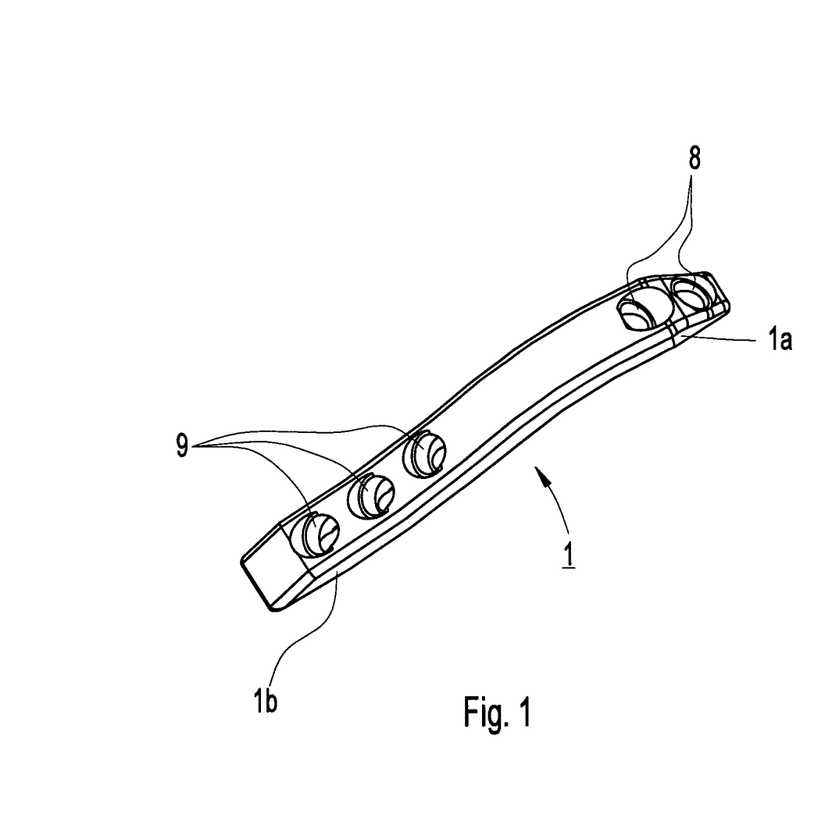
FIGS. 1 and 2 are views in perspective of a first version of a substantially platelike body which forms part of the device according to the present invention.
Figure 2:
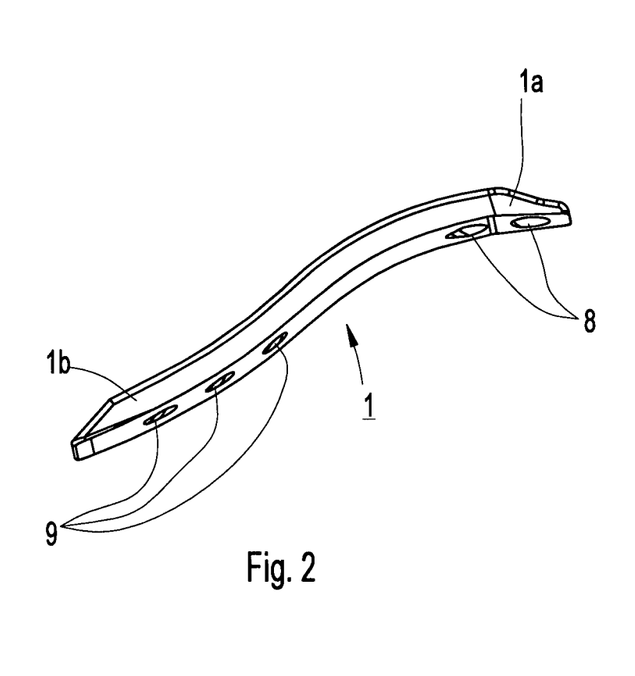
Figure 3:
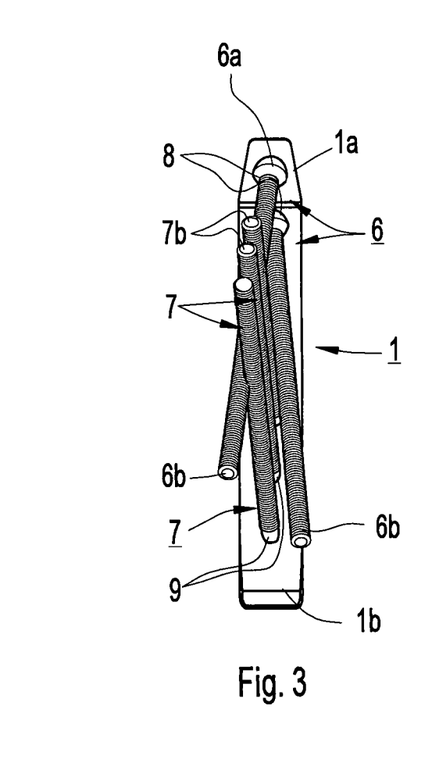
FIGS. 3-7 illustrate in various views the substantially platelike body according to FIGS. 1 and 2 with fixing elements inserted in it which are also part of the device according to the present invention.
Figure 4:
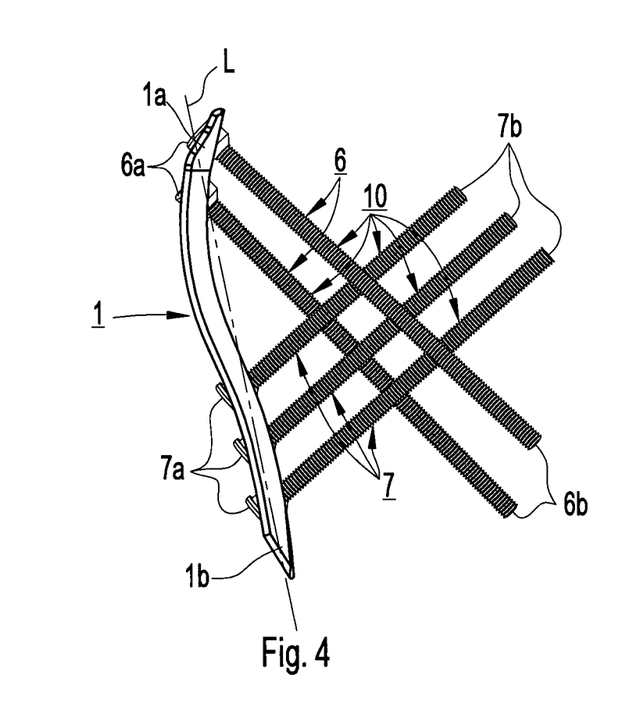
Figure 5:
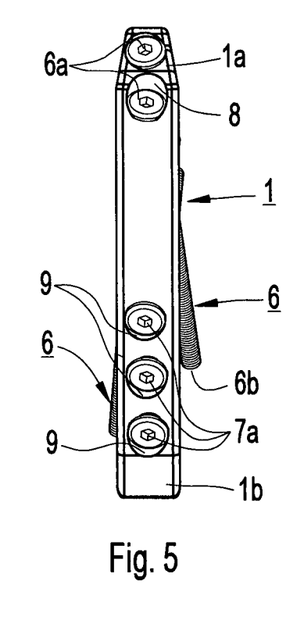
Figure 6:
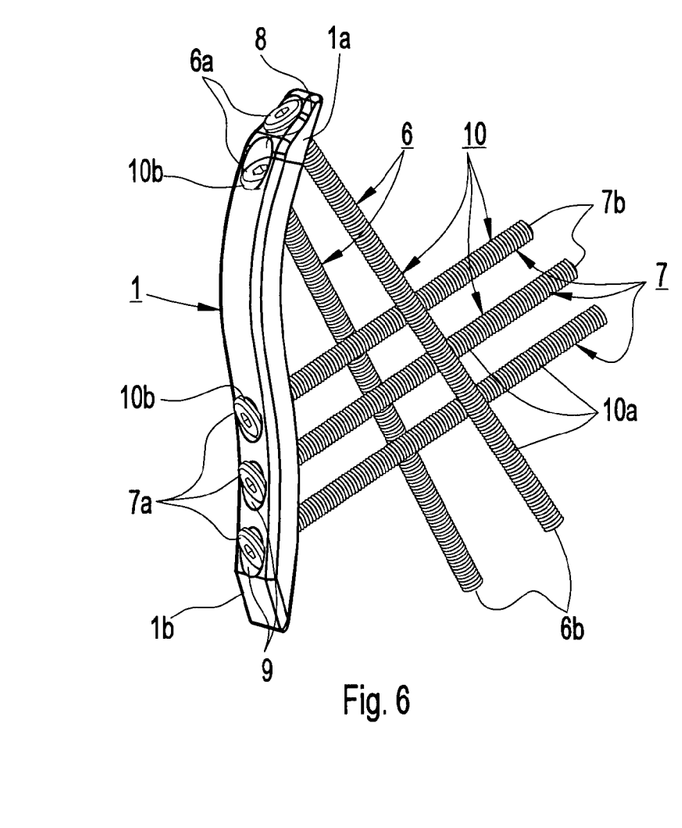
Figure 7:
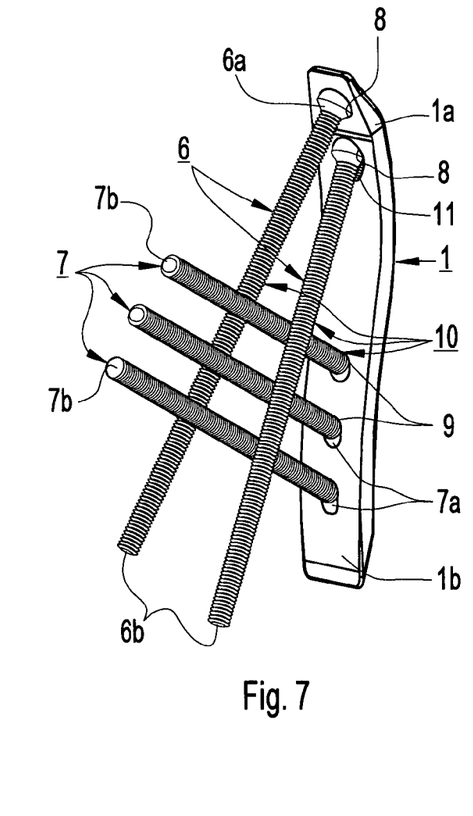
Figure 8:
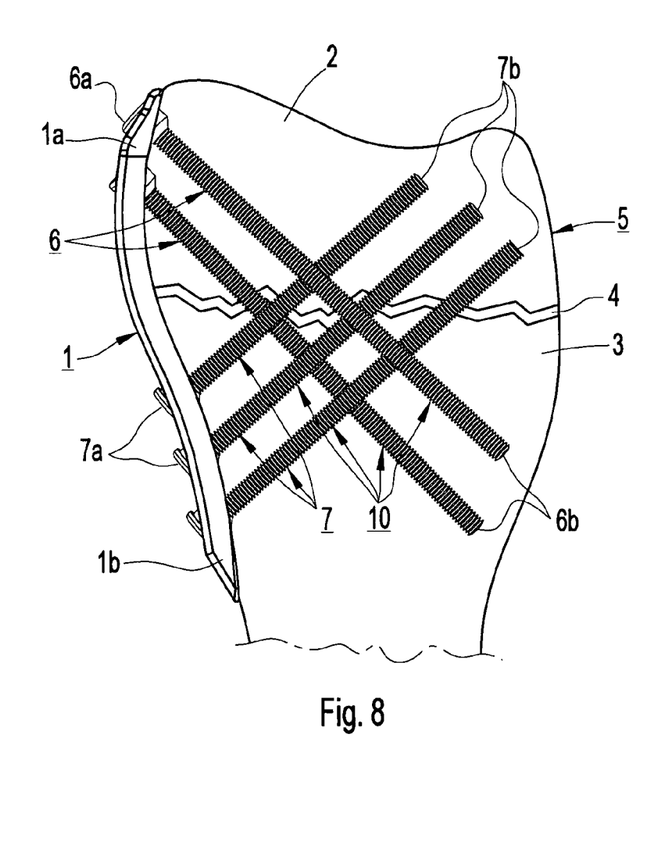
FIG. 8 depicts in schematic sideview the device according to the present invention after it has been fitted to a radius fracture.
Figure 9:
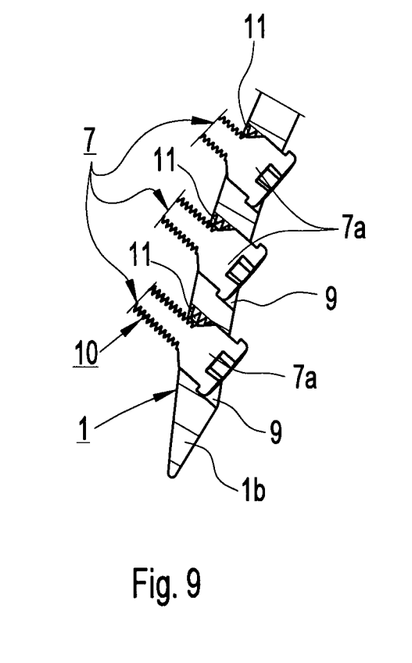
FIG. 9 is an enlarged cutaway view of a proximal end portion of the substantially platelike body with fixing elements inserted in it.

Preferably, at least one of the distal fixing elements 6 and at least one of the proximal fixing elements 7 cross substantially the centre of the radius fracture 4 (see FIG. 8).

The predrilled holes 8, 9 may as necessary and desired run obliquely at the same or substantially the same or at different angles relative to the longitudinal axis L of the body 1. Good fixation results are achieved if the predrilled holes 8 in the distal end portion 1a of the body 1 run obliquely at substantially an angle of 45° relative to the body's longitudinal axis L, while the predrilled holes 9 in the body's proximal end portion 1b run obliquely at an angle of about 45-60°, substantially an angle of 45-50°, relative to the body's longitudinal axis. The predrilled holes 8 and 9 in the respective end portions 1a, 1b thus run, as is also to be preferred, substantially parallel with one another as viewed in the transverse direction of the body. The fixing elements 6, 7 in the respective end portions 1a, 1b will thus also, as viewed in the transverse direction of the body, run parallel with one another.

According to the invention, the predrilled holes 8, 9 with advantage also run obliquely relative to the longitudinal axis L of the body 1 so that the fixing elements 6 introduced through holes 8 in the body's distal end portion 1a cross the fixing elements 7 introduced through holes 9 in the body's proximal end portion 1b.

According to the first version depicted in the drawings of the device according to the present invention, the predrilled holes 9 in the proximal end portion 1b of the body 1 run obliquely relative to the body's longitudinal axis L so that fixing elements 7 introduced through them are situated in a substantially common plane which is oriented substantially in the body's longitudinal direction as viewed in the longitudinal direction of the body (see preferably FIGS. 3-7).

Correspondingly, according to the same version, the predrilled holes 8 in the distal end portion 1a of the body 1 run obliquely relative to the body's longitudinal axis L so that fixing elements 6 introduced through them are situated in different planes as viewed in the longitudinal direction of the body (FIGS. 3-7).

Accordingly, the planes in which the distal fixing elements 6 are situated run at angles relative to the plane in which the proximal fixing elements 7 are situated and relative to one another as viewed in the longitudinal direction of the body 1. The planes in which the distal fixing elements 6 are situated thus run on respective sides of the plane in which the proximal fixing elements 7 are situated. The angles of the planes for the distal fixing elements 6 on respective sides of the plane for the proximal fixing elements 7 in the version depicted are equal relative to the last-mentioned planes.

Figure 10:
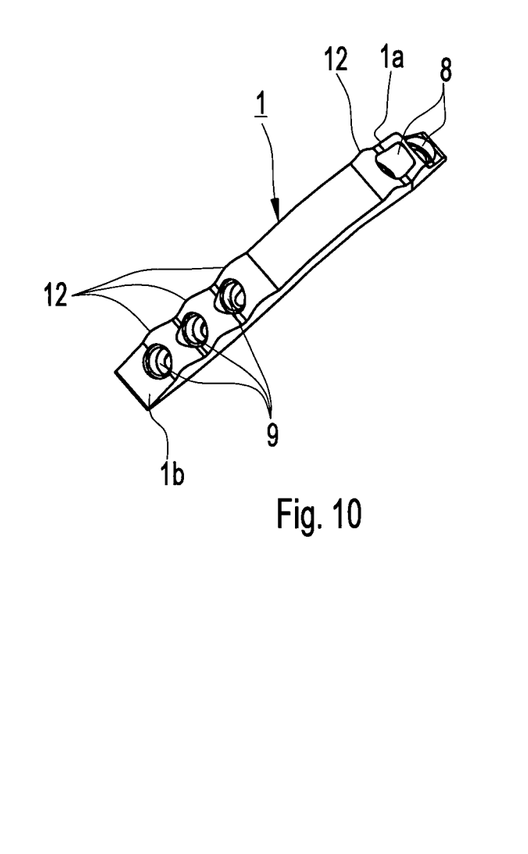
FIGS. 10 and 11 are views in perspective of a second version of a substantially platelike body which forms part of the device according to the present invention.
Figure 11:
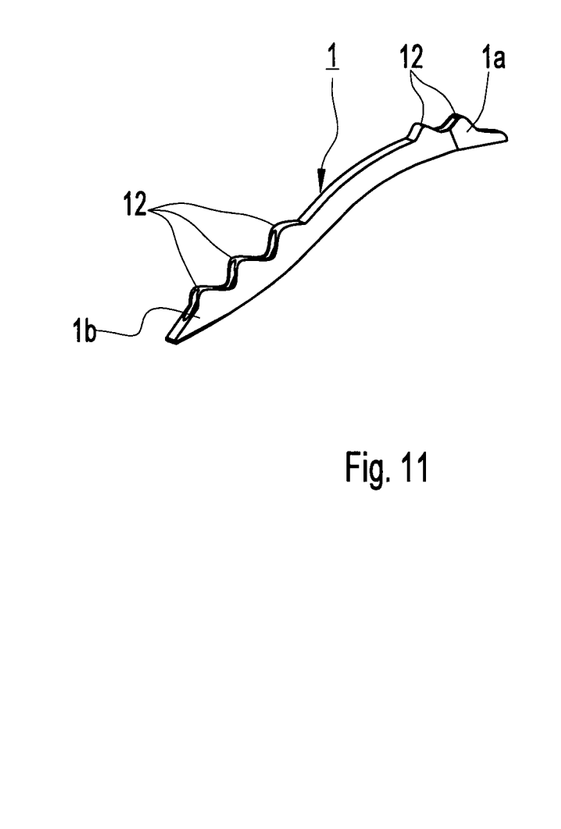

If its thickness is about 2 mm, the body 1 is of undulating shape in the region of each distal and proximal hole 8, 9, so that any heads 6a, 7a of the fixing elements 6, 7 should not protrude above the body (see FIGS. 10 and 11). These undulating portions are designated by ref. 12 in FIGS. 10 and 11. If the body 1 has a thickness of 3 mm, the heads 6a, 7a of the fixing elements 6, 7 may be countersunk in it and it need not be provided with any undulating portions.

The expression "fixing elements" as used here means screws, pins, etc. which may be of circular or some other, e.g. triangular, quadrilateral or other polygonal, cross-section.

Each fixing element 6, 7 has according to the present invention at least one fixing portion 10 for locking the fixing element in the bone fragments 2, 3 in the radius fracture 4 and for locking the fixing element to the body 1, thereby achieving effective fixation of the radius fracture.

The fixing portion 10 of each fixing element 6, 7 may assume any shape appropriate to purpose.

The fixing portion may for example take the form of a threaded portion 10 for screwing the fixing element 6, 7 into the bone fragments 2, 3 and into the elongate body 1. For effective compression of the bone fragments 2, 3 against one another and of the body 1 against the bone fragments, the threaded portion 10 may be provided with threads whose pitch varies in the longitudinal direction of the fixing element 6, 7 in such a way that it increases towards the respective tip 6b, 7b of the fixing element.

The fixing portion 10 of the fixing element 6, 7 may alternatively take the form of two separate threaded portions 10a and 10b, viz. a first threaded portion 10a configured for screwing into the bone fragments 2, 3 and a second threaded portion 10b configured for screwing into the body 1. As in the first version, the pitch of the threads of the two threaded portions 10a, 10b may vary, in which case the achievement of desired compression of the body 1 against the bone fragments 2, 3 entails the pitch of the threads (on the first threaded portion 10a) which cooperate with the bone fragments 2, 3 being greater than the pitch of the threads (on the second threaded portion 10b) which cooperate with the body 1.

Compression of the bone fragments towards one another is also possible if the first threaded portion 10a cooperates only with whichever of said bone fragments 2, 3 (bone fragment 2 or 3) is further away from the body 1 or if the pitch of the threads on the first threaded portion varies in its longitudinal direction in such a way that the pitch increases towards the tip 6b, 7b of the fixing element.

In cases where, as in FIGS. 3-9, the fixing elements 6, 7 have a pronounced head 6a, 7a, the latter may constitute said second threaded portion 10b for screwing into the body 1.

The predrilled holes 8, 9 in the body 1 may be configured without threads, in which case the threaded portion 10 or portions 10a, 10b of the fixing elements 6, 7 will cut threads in the body 1 when they are screwed into it.

Alternatively, the predrilled holes 8, 9 in the body 1 may be provided with threads 11 adapted to the threads on the fixing elements 6, 7, i.e. the threaded portion 10 of the fixing elements, or on at least their second threaded portion 10b.

In brief, the fixation of a bone fracture 4, in particular a fracture in the radius 5, by means of the device described above, may for example be effected as follows:

An incision of about 40-50 mm or two shorter incisions of about 20 mm each are made at a given location/locations relative to the fracture. After the making of the incision/incisions, the body 1 is positioned correctly relative to the radius fracture 4, i.e. the body is placed running in the longitudinal direction transversely across the fracture, and the predrilled holes 8, 9 in the body which are to be used are determined. The positioning of the body 1 may be facilitated by using for the introduction of the body into, for example, the incision distal to the fracture 4 a tubular element (not depicted) which is screwed into one of the distal holes 8 in the body as a guidance aid which can be taken hold of and used as a kind of "handle" for moving the body along the radius 5 and guiding it correctly towards the incision proximal to the fracture. If so desired, the tubular element may thereafter also be used as a guidance aid for a drill for making a hole in the bone fragments 2, 3 for a distal fixing element 6. Alternatively, a distal fixing element may be introduced, e.g. by being screwed in, directly into the bone fragments 2, 3. When using a drill for making a hole in the bone fragments 2, 3 for a distal fixing element 6, it is possible with advantage to apply a measuring rod (not depicted) to the drill in order to monitor the depth of the hole before the fixing element is fitted. The body 1 being chamfered at at least one, here at least the proximal, end portion 1b, but preferably at both end portions 1a, 1b, facilitates the movement of the body along the radius 5 from the distal incision towards the radial steloid to the incision proximal to the fracture 4. The fracture 4 is stabilised in a suitable manner. After the removal of any tubular element and drill, a first distal fixing element 6 is introduced, e.g. by screwing in, into a hole 8 intended for the purpose in the distal end portion 1a of the body 1. The body 1 or the body and the hole made by the drill in the bone fragments 2, 3 serves/serve as a kind of drilling guide or as a guidance aid, and with a fixing element 6 of correctly adapted length it is possible by means of, for example, a manoeuvring element to continue screwing in the threaded fixing portion 10 of the fixing element or to start screwing in the second threaded portion 10b of the fixing portion 10 of the fixing element into the body, so that the fixing element is driven into the radius distally to the fracture 4 and proceeds through the fracture and into the bone proximal to the fracture. The screwing in continues with advantage until the fixing element 6 penetrates the cortex on the far side of the radius 5 from the fixation device. The whole process is monitored by radiography. It is important that the body 1 be kept parallel with the longitudinal axis of the bone 5 during the screwing in.

After any resetting of the radius fracture 4 and adjustment proximally of the body 1, the first proximal fixing element 7 is driven into the radius proximally to the fracture 4 and proceeds through the fracture and the bone distally to the fracture, crossing the first distal fixing element 6. The procedure for driving in and fixing the distal fixing element 6 as above is substantially repeated, with or without the aforesaid tubular element as guidance aid and the aforesaid drill for drilling out a further hole in the bone fragments 2, 3 in the radius fracture 4, but preferably without the proximal fixing element 7 penetrating the cortex on the far side of the radius 5 from the fixation device.

Introducing and fixing a second distal fixing element 6 and a second proximal fixing element 7 respectively in suitable holes 8 and 9 for them in the body 1, and driving said fixing elements into the radius 5, are effected in the same way as above, resulting in stable fixation of the fracture 4 in the radius.

The operation is concluded by suturing and bandaging the surgical wound.

It will be obvious to one skilled in the art that the device according to the present invention can be altered and modified within the scope of the claims set out below without departing from the idea and objects of the invention. Thus, as indicated above, the shape and size of the device and its constituent parts may vary depending on how the device is to be used, i.e. whether the patient is a child or an adult, the patient's anatomy, how many fixing elements are to be used and at what angle relative to the fracture, etc. The choice of materials for the various parts of the device may also vary.

The invention claimed is:

1. A device for internal fixation of bone fragments (2, 3) in a radius fracture (4),
   which device comprises at least one body (1) for abutment against the bone fragments (2, 3) in the radius fracture (4), and a plurality of fixing elements including at least two distal and at least two proximal fixing elements (6, 7) which are intended to be locked to the body for fixation of said bone fragments,
   which body (1) has a plurality of predrilled holes, the body having, in a distal end portion (1a) at least two predrilled holes (8) for the distal fixing elements (6), and in a proximal end portion (1b) at least two predrilled holes (9) for the proximal fixing elements (7), the distal end portion and the proximal end portion of the body engaging the bone fragments on opposite sides of the radius fracture when the body abuts against the bone fragments,
   wherein all of the predrilled holes (8, 9) run obliquely relative to a longitudinal axis (L) of the body (1) so that all of the fixing elements (6, 7) which, after abutment of the body against the bone fragments (2, 3) in the radius fracture (5), are introduced into said bone fragments through holes (8, 9) in the body's distal end portion (1a) and proximal end portion (1b) cross the radius fracture as viewed in the transverse direction of the body when the body abuts against the bone fragments, and
   each fixing element (6, 7) has at least one fixing portion (10; 10a, 10b) for locking the fixing element in the bone fragments (2, 3) in the radius fracture (4) and for locking the fixing element to the body (1); and
   all of the predrilled holes (9) in the proximal end portion (1b) of the body (1) run obliquely relative to the body's longitudinal axis (L) so that all of the proximal fixing elements (7) introduced through them are situated, as viewed in the body's longitudinal direction, in a common plane which is oriented in the body's longitudinal direction, and
   all of the predrilled holes (8) in the distal end portion (1a) of the body (1) run obliquely relative to the body's longitudinal axis (L) so that each of the distal fixing elements (6) introduced through them are situated in different planes as viewed in the body's longitudinal direction, and
   the planes in which the distal fixing elements (6) are situated run at angles relative to the plane in which the proximal fixing elements (7) are situated and relative to one another as viewed in the longitudinal direction of the body (1), wherein all of the predrilled holes (8, 9) run obliquely relative to the longitudinal axis (L) of the body (1) so that the distal fixing elements (6) introduced through the predrilled holes (8) in the body's distal end portion (1a) cross, as viewed in the transverse direction of the body, the proximal fixing elements (7) introduced through the predrilled holes (9) in the body's proximal end portion (1b).

2. A device according to claim 1, wherein the predrilled holes (8, 9) are arranged in the body (1), as viewed in the body's longitudinal direction, in a common plane.

3. A device according to claim 1, wherein at least one of the distal fixing elements (6) and at least one of the proximal fixing elements (7) cross the centre of the radius fracture (4).

4. A device according to claim 1, wherein the predrilled holes (8) in the distal end portion (1a) of the body (1) run obliquely at angles of 45° relative to the body's longitudinal axis (L), while the predrilled holes (9) in the body's proximal end portion (1b) run obliquely at angles of 45-50° relative to the body's longitudinal axis.

5. A device according to claim 1, wherein the predrilled holes (8, 9) in the respective end portions (1a, 1b) of the body (1) run parallel with one another as viewed in the transverse direction of the body.

6. A device according to claim 1, wherein the planes in which the distal fixing elements (6) are situated run, on respective sides of the plane in which the proximal fixing elements (7) are situated, at angles relative thereto in the longitudinal direction of the body (1).

7. A device according to claim 6, wherein the planes in which the distal fixing elements (6) are situated run, on respective sides of the plane in which the proximal fixing elements (7) are situated, at the same angles relative thereto in the longitudinal direction of the body (1).

8. A device according to claim 1, wherein the body (1) has a thickness of about 3 mm.

9. A device according to claim 1, wherein the body (1) has a thickness of about 2 mm and is of substantially undulating shape (12) in the region of each predrilled distal or proximal hole (8, 9).

10. A device according to claim 1, wherein the body (1) has a curved shape in its longitudinal direction.

11. A device according to claim 1, wherein one or both of the end portions (1a, 1b) of the body (1) is/are chamfered.

12. A device according to claim 1, wherein the fixing portion of each fixing element (6, 7) takes the form of a threaded portion (10) for screwing the fixing element into said bone fragments (2,3) and into said body (1).

13. A device according to claim 12, wherein the threaded portion (10) is provided with threads whose pitch varies in the longitudinal direction of the fixing element (6, 7) in such a way that the pitch increases towards the tip (6b, 7b) of the fixing element.

14. A device according to claim 1, wherein the fixing portion (10) of each fixing element (6, 7) takes the form of two separate threaded portions (10a, 10b), viz. a first threaded portion (10a) configured for screwing into said bone fragments (2, 3) and a second threaded portion (10b) configured for screwing into said body (1).

15. A device according to claim 14, wherein the pitch of the threads on the two threaded portions (10a, 10b) varies so that the pitch of the threads which cooperate with said bone fragments (2, 3) is greater than the pitch of the threads which cooperate with said body (1).

16. A device according to claim 14, wherein the pitch of the threads on the first threaded portion (10a) varies in the longitudinal direction of said first threaded portion in such a way that the pitch increases towards the tip (6b, 7b) of the fixing element (6, 7).

17. A device according to claim 1, wherein said fixing elements (6, 7) take the form of screws or pins, each with at least one fixing portion.

18. A device according to claim 12, wherein the predrilled holes (8, 9) in the body (1) have no threads and said fixing elements (6, 7) cut threads in the body when they are screwed into it.

19. A device according to claim 12, wherein the predrilled holes (8, 9) in the body (1) have threads (11) adapted to the threads on the fixing elements (6, 7).

20. A device according to claim 1, wherein the predrilled holes (8, 9) in the body (1) have threads (11) adapted to threads on tubular guidance aids which can be fitted in the holes, for positioning of the body for abutment against the bone fragments (2, 3) in the radius fracture (4) and for drills for making holes for the fixing elements (6, 7) in the bone fragments (2, 3) in the radius fracture (4).

21. A device according to claim 1, wherein the body (1) is made of polyethylene.

* * * * *